(12) United States Patent
Fallin et al.

(10) Patent No.: US 7,625,393 B2
(45) Date of Patent: *Dec. 1, 2009

(54) APPARATUS AND METHOD FOR DYNAMIC VERTEBRAL STABILIZATION

(75) Inventors: T. Wade Fallin, Hyde Park, UT (US); Daniel E. Gerbec, Logan, UT (US); Joel Dever, Millville, UT (US)

(73) Assignee: Stryker Spine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/070,256

(22) Filed: Feb. 15, 2008

(65) Prior Publication Data

US 2009/0099607 A1 Apr. 16, 2009

Related U.S. Application Data

(63) Continuation of application No. 11/087,115, filed on Mar. 22, 2005, now Pat. No. 7,361,196.

(60) Provisional application No. 60/655,298, filed on Feb. 22, 2005.

(51) Int. Cl.
*A61B 17/70* (2006.01)
(52) U.S. Cl. .................................... 606/247
(58) Field of Classification Search .................. 606/61, 606/246–248; 623/17.11–17.16
See application file for complete search history.

(56) References Cited

U.S. PATENT DOCUMENTS

| 4,369,769 A | 1/1983 | Edwards |
|---|---|---|
| 4,743,260 A | 5/1988 | Burton |
| 5,034,011 A | 7/1991 | Howland |
| 5,092,866 A | 3/1992 | Breard et al. |
| 5,180,393 A | 1/1993 | Commarmond et al. |
| 5,282,863 A | 2/1994 | Burton |
| 5,375,823 A | 12/1994 | Navas et al. |
| 5,415,661 A | 5/1995 | Holmes |
| 5,456,722 A | 10/1995 | McLeod et al. |
| 5,480,401 A | 1/1996 | Navas et al. |

(Continued)

FOREIGN PATENT DOCUMENTS

| DE | 2821678 | 11/1979 |
|---|---|---|

(Continued)

OTHER PUBLICATIONS

U.S. Appl. No. 11/087,434.
U.S. Appl. No. 11/589,648.
U.S. Appl. No. 11/589,512.

*Primary Examiner*—Bruce E Snow
(74) *Attorney, Agent, or Firm*—Lerner, David, Littenberg, Krumholz & Mentlik, LLP

(57) ABSTRACT

A posterior vertebral stabilizer has a resilient member such as a linear spring, which operates in tension and compression. The resilient member may be kept straight by a stabilization rod extending through the spring, or by a telescoping assembly that encases the resilient member. The ends of the stabilizer are attachable to pedicles of adjacent vertebrae so that the stabilizer adds stiffness to control flexion and extension of the vertebrae. Two such stabilizers may be used, and may be connected together by a crosslink designed to limit relative rotation of the stabilizers. Thus, the stabilizers may restrict axial rotation and lateral bending between the vertebrae, while permitting stiffened flexion and extension. Such stabilizers help provide the stiffness of a healthy intervertebral disc. In the event that fusion of the joint becomes necessary, a set screw or other component may be used to further restrict flexion and extension.

21 Claims, 10 Drawing Sheets

U.S. PATENT DOCUMENTS

| | | | |
|---|---|---|---|
| 5,496,318 | A | 3/1996 | Howland et al. |
| 5,540,688 | A | 7/1996 | Navas et al. |
| 5,562,737 | A | 10/1996 | Graf et al. |
| 5,609,634 | A | 3/1997 | Voydeville et al |
| 5,645,599 | A | 7/1997 | Samani et al. |
| 5,672,175 | A | 9/1997 | Martin et al. |
| 5,704,936 | A | 1/1998 | Mazel et al. |
| 5,725,582 | A | 3/1998 | Bevan et al. |
| 5,749,873 | A | 5/1998 | Fairley et al. |
| 5,836,948 | A | 11/1998 | Zucherman et al. |
| 5,860,977 | A | 1/1999 | Zucherman et al. |
| 5,876,404 | A | 3/1999 | Zucherman et al. |
| RE36,221 | E | 6/1999 | Breard et al. |
| 5,961,516 | A | 10/1999 | Graf et al. |
| 5,986,169 | A | 11/1999 | Gjunter et al. |
| 6,048,342 | A | 4/2000 | Zucherman et al. |
| 6,068,630 | A | 5/2000 | Zucherman et al. |
| 6,074,390 | A | 6/2000 | Zucherman et al. |
| 6,090,112 | A | 7/2000 | Zucherman et al. |
| 6,149,652 | A | 11/2000 | Zucherman et al. |
| 6,152,926 | A | 11/2000 | Zucherman et al. |
| 6,156,038 | A | 12/2000 | Zucherman et al. |
| 6,176,881 | B1 | 1/2001 | Schar et al. |
| 6,183,471 | B1 | 2/2001 | Zucherman et al. |
| 6,190,387 | B1 | 2/2001 | Zucherman et al. |
| 6,235,030 | B1 | 5/2001 | Zucherman et al. |
| 6,238,397 | B1 | 5/2001 | Zucherman et al. |
| 6,241,730 | B1 | 6/2001 | Alby et al. |
| 6,267,764 | B1 | 7/2001 | Elberg |
| 6,280,444 | B1 | 8/2001 | Zucherman et al. |
| 6,290,700 | B1 | 9/2001 | Schmotzer et al. |
| 6,293,949 | B1 | 9/2001 | Justis et al. |
| 6,296,644 | B1 | 10/2001 | Saurat et al. |
| 6,332,882 | B1 | 12/2001 | Zucherman et al. |
| 6,332,883 | B1 | 12/2001 | Zucherman et al. |
| 6,379,355 | B1 | 4/2002 | Zucherman et al. |
| 6,402,750 | B1 | 6/2002 | Atkinson et al. |
| 6,419,676 | B1 | 7/2002 | Zucherman et al. |
| 6,419,677 | B2 | 7/2002 | Zucherman et al. |
| 6,423,065 | B2 | 7/2002 | Ferree |
| 6,440,169 | B1 | 8/2002 | Elberg et al. |
| 6,451,019 | B1 | 9/2002 | Zucherman et al. |
| 6,451,020 | B1 | 9/2002 | Zucherman et al. |
| 6,471,704 | B2 | 10/2002 | Gertzbein et al. |
| 6,478,796 | B2 | 11/2002 | Zucherman et al. |
| 6,500,178 | B2 | 12/2002 | Zucherman et al. |
| 6,514,256 | B2 | 2/2003 | Zucherman et al. |
| 6,582,433 | B2 | 6/2003 | Yun |
| 6,585,769 | B1 | 7/2003 | Muhanna et al. |
| 6,616,669 | B2 | 9/2003 | Ogilvie et al. |
| 6,626,944 | B1 | 9/2003 | Taylor et al. |
| 6,652,527 | B2 | 11/2003 | Zucherman et al. |
| 6,652,534 | B2 | 11/2003 | Zucherman et al. |
| 6,652,585 | B2 | 11/2003 | Lange |
| 6,695,842 | B2 | 2/2004 | Zucherman et al. |
| 6,699,246 | B2 | 3/2004 | Zucherman et al. |
| 6,699,247 | B2 | 3/2004 | Zucherman et al. |
| 6,733,534 | B2 | 5/2004 | Sherman |
| 6,761,719 | B2 | 7/2004 | Justis et al. |
| 6,761,720 | B1 | 7/2004 | Senegas et al. |
| 6,783,527 | B2 | 8/2004 | Drewry et al. |
| 6,796,983 | B1 | 9/2004 | Zucherman et al. |
| 6,802,844 | B2 | 10/2004 | Ferree |
| 6,835,205 | B2 | 12/2004 | Atkinson et al. |
| 6,835,207 | B2 | 12/2004 | Zacouto et al. |
| 7,022,138 | B2 | 4/2006 | Mashburn |
| 7,029,475 | B2 | 4/2006 | Panjabi |
| 7,361,196 | B2 * | 4/2008 | Fallin et al. ............ 623/61 |
| 2001/0007073 | A1 | 7/2001 | Zucherman et al. |
| 2001/0012938 | A1 | 8/2001 | Zucherman et al. |
| 2001/0016743 | A1 | 8/2001 | Zucherman et al. |
| 2001/0021850 | A1 | 9/2001 | Zucherman et al. |
| 2001/0031965 | A1 | 10/2001 | Zucherman et al. |
| 2001/0039452 | A1 | 11/2001 | Zucherman et al. |
| 2002/0091446 | A1 | 7/2002 | Zucherman et al. |
| 2002/0116000 | A1 | 8/2002 | Zucherman et al. |
| 2002/0133155 | A1 | 9/2002 | Ferree |
| 2002/0143331 | A1 | 10/2002 | Zucherman et al. |
| 2002/0151978 | A1 | 10/2002 | Zacouto et al. |
| 2002/0183746 | A1 | 12/2002 | Zucherman et al. |
| 2003/0009226 | A1 | 1/2003 | Graf |
| 2003/0065330 | A1 | 4/2003 | Zucherman et al. |
| 2003/0109880 | A1 | 6/2003 | Shirado et al. |
| 2003/0171749 | A1 | 9/2003 | Le Couedic et al. |
| 2003/0191470 | A1 | 10/2003 | Ritland |
| 2003/0220642 | A1 | 11/2003 | Freudiger |
| 2003/0220643 | A1 | 11/2003 | Ferree |
| 2004/0006341 | A1 | 1/2004 | Shaolian et al. |
| 2004/0024458 | A1 | 2/2004 | Senegas et al. |
| 2004/0049189 | A1 | 3/2004 | Le Couedic et al. |
| 2004/0049190 | A1 | 3/2004 | Biedermann et al. |
| 2004/0073215 | A1 | 4/2004 | Carli |
| 2004/0078082 | A1 | 4/2004 | Lange |
| 2004/0082954 | A1 | 4/2004 | Teitelbaum et al. |
| 2004/0087950 | A1 | 5/2004 | Teitelbaum |
| 2004/0106995 | A1 | 6/2004 | Le Couedic et al. |
| 2004/0116927 | A1 | 6/2004 | Graf |
| 2004/0117017 | A1 | 6/2004 | Pasquet et al. |
| 2004/0143264 | A1 | 7/2004 | McAfee |
| 2004/0147928 | A1 | 7/2004 | Landry et al. |
| 2004/0153071 | A1 | 8/2004 | Zucherman et al. |
| 2004/0167520 | A1 | 8/2004 | Zucherman et al. |
| 2004/0172025 | A1 | 9/2004 | Drewry et al. |
| 2004/0181282 | A1 | 9/2004 | Zucherman et al. |
| 2004/0181285 | A1 | 9/2004 | Simonson |
| 2004/0215191 | A1 | 10/2004 | Kitchen |
| 2004/0220568 | A1 | 11/2004 | Zucherman et al. |
| 2004/0225289 | A1 | 11/2004 | Biedermann et al. |
| 2004/0236327 | A1 | 11/2004 | Paul et al. |
| 2004/0236328 | A1 | 11/2004 | Paul et al. |
| 2004/0236329 | A1 | 11/2004 | Panjabi |
| 2004/0243239 | A1 | 12/2004 | Taylor |
| 2004/0267260 | A1 | 12/2004 | Mack et al. |
| 2005/0010293 | A1 | 1/2005 | Zucherman et al. |
| 2005/0010298 | A1 | 1/2005 | Zucherman et al. |
| 2005/0033295 | A1 | 2/2005 | Wisnewski |
| 2005/0049708 | A1 | 3/2005 | Atkinson et al. |
| 2005/0056979 | A1 | 3/2005 | Studer et al. |
| 2005/0065514 | A1 | 3/2005 | Studer |
| 2005/0065515 | A1 | 3/2005 | Jahng |
| 2005/0065516 | A1 | 3/2005 | Jahng |
| 2005/0085815 | A1 | 4/2005 | Harms et al. |
| 2005/0143737 | A1 | 6/2005 | Pafford et al. |
| 2005/0143823 | A1 | 6/2005 | Boyd et al. |
| 2005/0154390 | A1 | 7/2005 | Biedermann et al. |
| 2005/0171543 | A1 | 8/2005 | Timm et al. |
| 2005/0177156 | A1 | 8/2005 | Timm et al. |
| 2005/0182400 | A1 | 8/2005 | White |
| 2005/0182401 | A1 | 8/2005 | Timm et al. |
| 2005/0203519 | A1 | 9/2005 | Harms et al. |
| 2005/0222569 | A1 | 10/2005 | Panjabi |
| 2005/0245930 | A1 | 11/2005 | Timm et al. |
| 2005/0261682 | A1 | 11/2005 | Ferree |
| 2005/0288670 | A1 | 12/2005 | Panjabi et al. |
| 2006/0015100 | A1 | 1/2006 | Panjabi et al. |
| 2006/0036240 | A1 | 2/2006 | Colleran et al. |
| 2006/0064090 | A1 | 3/2006 | Park |
| 2006/0189983 | A1 | 8/2006 | Fallin et al. |
| 2006/0189984 | A1 | 8/2006 | Fallin et al. |

FOREIGN PATENT DOCUMENTS

| | | |
|---|---|---|
| DE | 94 19 900 U1 | 4/1996 |
| DE | 10320417 | 12/2004 |

| | | | | | |
|---|---|---|---|---|---|
| EP | 0 322 334 | 6/1989 | WO | 01/91658 | 12/2001 |
| EP | 0 669 109 | 8/1995 | WO | 01/95818 | 12/2001 |
| EP | 0 677 277 | 10/1995 | WO | 02/03882 | 1/2002 |
| EP | 0 768 843 | 4/1997 | WO | 02/07621 | 1/2002 |
| EP | 1 239 785 | 9/2002 | WO | 02/07622 | 1/2002 |
| EP | 1 343 424 | 9/2003 | WO | 02/07623 | 1/2002 |
| EP | 1 399 078 | 3/2004 | WO | 02/30336 | 4/2002 |
| FR | 2 680 461 A1 | 2/1993 | WO | 02/051326 | 7/2002 |
| FR | 2 704 137 | 10/1994 | WO | 02/067792 | 9/2002 |
| FR | 2 717 370 | 9/1995 | WO | 02/067793 | 9/2002 |
| FR | 2 738 143 | 3/1997 | WO | 02/102259 | 12/2002 |
| FR | 2 778 089 A1 | 11/1999 | WO | 03/015646 | 2/2003 |
| FR | 2 799 949 | 4/2001 | WO | 03/045262 | 6/2003 |
| FR | 2 809 304 | 11/2001 | WO | 03/077806 | 9/2003 |
| FR | 2 810 533 | 12/2001 | WO | 2004/017817 A2 | 3/2004 |
| FR | 2 843 538 | 2/2004 | WO | 2004/019762 | 3/2004 |
| GB | 2382304 | 5/2003 | WO | 2004/024010 | 3/2004 |
| JP | 10-277070 | 10/1998 | WO | 2004/024011 | 3/2004 |
| WO | 94/21185 | 9/1994 | WO | 2004/032794 | 4/2004 |
| WO | 95/05783 | 3/1995 | WO | 2004/039239 | 5/2004 |
| WO | 97/32533 | 9/1997 | WO | 2004/039243 | 5/2004 |
| WO | 98/22033 | 5/1998 | WO | 2004/041066 | 5/2004 |
| WO | 99/21500 | 5/1999 | WO | 2004/073533 | 9/2004 |
| WO | 99/21501 | 5/1999 | WO | 2004/098423 | 11/2004 |
| WO | 01/08574 A1 | 2/2001 | WO | 2004/098452 | 11/2004 |
| WO | 01/28442 | 4/2001 | WO | 2004/105577 | 12/2004 |
| WO | 01/45576 | 6/2001 | WO | 2004/105580 | 12/2004 |
| WO | 01/52758 A1 | 7/2001 | WO | 2004/110287 | 12/2004 |
| WO | 01/56481 | 8/2001 | WO | 2005/030066 | 4/2005 |
| WO | 01/64144 | 9/2001 | | | |
| WO | 01/91657 | 12/2001 | | | |

* cited by examiner

APPARATUS AND METHOD FOR DYNAMIC VERTEBRAL STABILIZATION

CROSS-REFERENCE TO RELATED APPLICATIONS

This application is a continuation of U.S. application Ser. No. 11/087,115, filed on Mar. 22, 2005, which claims the benefit of U.S. Provisional Application No. 60/655,298, filed Feb. 22, 2005, the disclosures of which are incorporated herein by reference.

BACKGROUND OF THE INVENTION

The present invention relates generally to orthopedic medicine, and more precisely, to systems and methods for restricting relative motion between vertebrae.

SUMMARY OF THE INVENTION

Many people experience back pain. Back pain is not only uncomfortable, but can be particularly debilitating.

Many people who wish to participate in sports, manual labor, or even sedentary employment are unable to do so because of pains that arise from motion of or pressure on the spinal column. Such pains are often caused by traumatic, inflammatory metabolic, synovial, neoplastic and degenerative disorders of the spine.

The intervertebral discs that separate adjacent vertebrae from each other serve to provide stiffness that helps to restrain relative motion of the vertebrae in flexion, extension, axial rotation, and lateral bending. However, a damaged disc may provide inadequate stiffness along one or more modes of spinal motion. Inadequate stiffness may result in excessive relative vertebral motion when the spine is under a given load, as when the patient uses the muscles of the back. Such excessive relative motion may cause further damage to the disc, thereby causing back pain and ultimately, requiring replacement of the disc and/or other operations to decompress nerves affected by central, lateral or foraminal stenosis.

Some stabilization devices have been proposed to restrict, but not entirely prevent, relative motion between adjacent vertebrae. Such devices are often somewhat complex and/or bulky. Many such devices cannot be tailored to limit the types of motion (i.e., flexion/extension, axial rotation, or lateral bending) that are most painful. Additionally, in the event that stabilization ultimately becomes insufficient, most known stabilization devices do not provide any mechanism that can be used to more fully secure the spinal motion segment.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to stabilize relative motion between two vertebrae. The present invention can be used as an alternative to spinal fusion to alleviate back pain resulting from traumatic, inflammatory, metabolic, synovial, neoplastic and degenerative spinal disorders. The configuration and operation of at least one embodiment of the invention will be shown and described in greater detail with reference to FIGS. 1 and 2, as follows.

In this application, the phrase "telescopic engagement" and variations thereof refer to two members, wherein a portion of one hollow member fits around a portion of a second member to permit relative linear motion of the two members. "Locking" of two members refers to substantially preventing relative translation or rotation between the members along at least one axis. "Generally symmetrical" refers to items that are arranged in a manner that is symmetrical or nearly symmetrical to each other, with no requirement of precise symmetry. For example, the left and right sides of the spinal column may be considered to be generally symmetrical, despite the fact that anatomical differences and asymmetries will exist between them. Two components that are "integrally formed" with each other are formed as a single piece.

Figure 1:
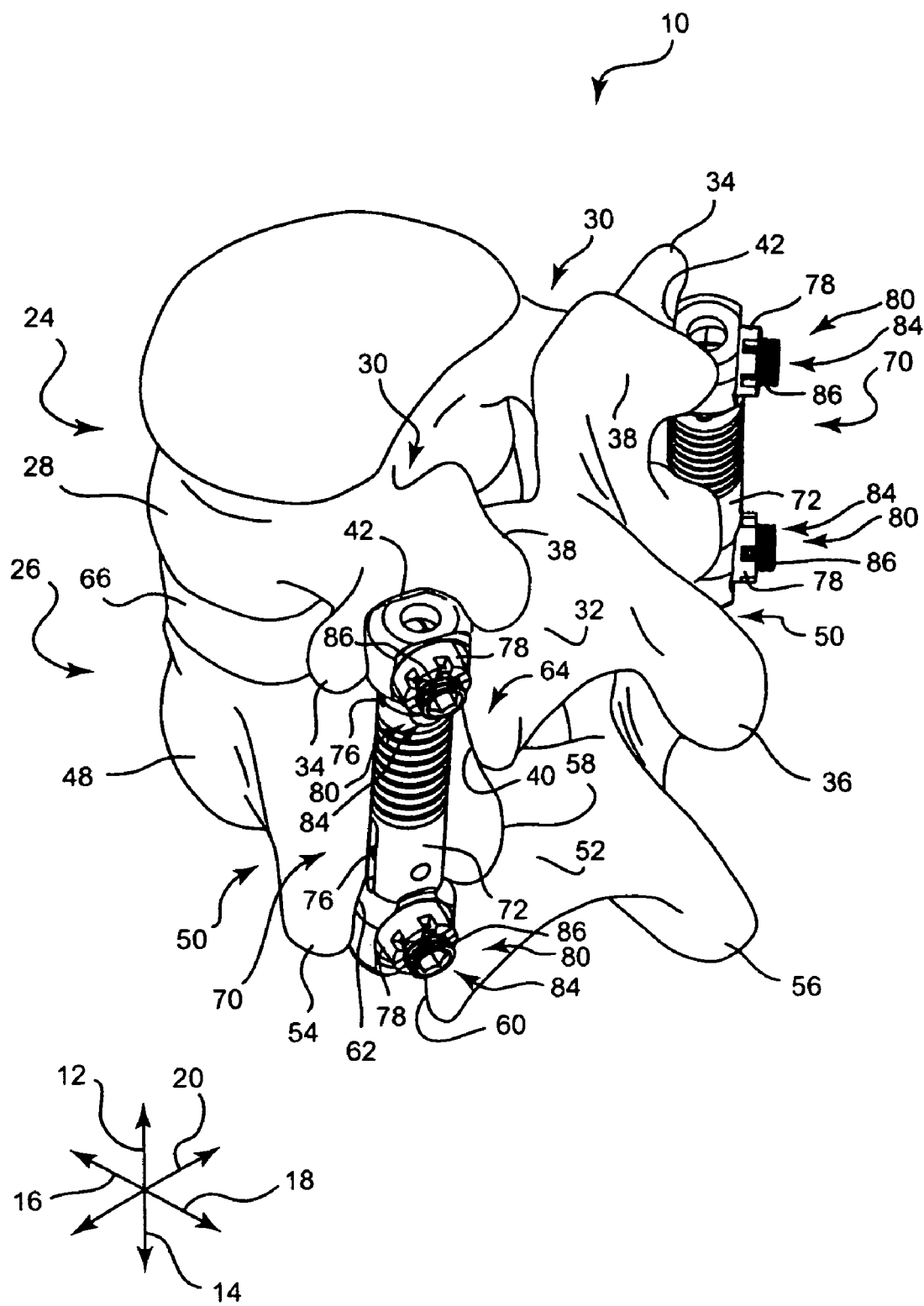
FIG. 1 is a perspective view of the L4 and L5 vertebrae of a spinal column, with left and right apparatus according to one embodiment of the invention attached to stabilize relative motion of the vertebrae.

Referring to FIG. 1, a perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral" refers to a position or orientation relatively further from the sagittal plane.

As shown, the portion of the spine 10 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods may be applicable to any vertebra or vertebrae of the spine 10 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. A posterior arch, or lamina 32, extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

The first vertebra 24 also has a pair of superior facets 38, which are positioned toward the top of the first vertebra 24 and face generally medially. Additionally, the first vertebra 24 has inferior facets 40, which are positioned toward the bottom of the first vertebra 24 and face generally laterally. Each of the pedicles 30 of the first vertebra 24 has a saddle point 42, which is positioned generally at the center of the juncture of each superior facet 38 with the adjacent transverse process 34.

Similarly, the second vertebra 26 has a body 48 from which two pedicles 50 extend posteriorly. A posterior arch, or lamina 52, extends between the posterior ends of the pedicles 50 to couple the pedicles 50 together. The second vertebra 26 also has a pair of transverse processes 54, each of which extends from the corresponding pedicle 50 generally along the medial/lateral axis 20, and a spinous process 56 that extends from the lamina 52 along the posterior direction 18.

The second vertebra 26 also has a pair of superior facets 58, which are positioned toward the top of the second vertebra 26 and face generally inward. Additionally, the second vertebra 26 has inferior facets 60, which are positioned toward the bottom of the second vertebra 26 and face generally outward. Each of the pedicles 60 of the second vertebra 26 has a saddle point 62, which is positioned generally at the center of the juncture of each superior facet 58 with the adjacent transverse process 54.

The superior facets 38 of the first vertebra 24 articulate (i.e., slide and/or press) with the inferior facets 60 of the second vertebra 26 to limit relative motion between the first and second vertebrae 24, 26. Thus, the combination of each superior facet 38 with the adjacent inferior facet 60 provides a facet joint 64. The first and second vertebrae 24, 26 thus define two facet joints 64 that span the distance between the first and second vertebrae 24, 26. The inferior facets 40 of the first vertebra 40 and the superior facets 58 of the second vertebra 26 are part of other facet joints that control motion between the first and second vertebrae 24, 26 and adjacent vertebrae (not shown) and/or the sacrum (also not shown). The vertebrae 24, 26 are separated from each other by an intervertebral disc 66.

As shown in FIG. 1, an apparatus 70 according to one embodiment of the invention is coupled to the vertebrae 24, 26 on either side of the sagittal plane to provide dynamic stabilization. In this application, "dynamic stabilization" refers to selectively limiting, but not entirely preventing, the relative motion of two objects. The apparatus 70 may be termed a "stabilizer."

As embodied in FIG. 1, the apparatus 70 is designed to preserve relatively free relative motion between the saddle points 42, 62 of the vertebrae 24, 26 along the cephalad and caudal directions 12, 14, thereby permitting flexion, extension, and lateral bending of the spine 10 with little restriction. However, the apparatus 70 is also designed to significantly restrict relative motion between the saddle points 42, 62 along the anterior direction 16, the posterior direction 18, and the medial/lateral axis 20. Accordingly, rotation of the spine 10 and relative anterior/posterior or medial/lateral motion of the vertebrae 24, 26 under shear are restricted.

As shown, each apparatus 70 has a bridge 72, a stabilization rod 74 (not visible in FIG. 1), a pair of pins 76, a pair of castle nuts 78, and a pair of fixation members 80. The fixation members 70 are implanted in the pedicles 30, 50 of the vertebrae 24, 26, respectively. More precisely, each of the fixation members 70 has a distal end (not shown) implanted in the pedicle 30 or 50 and a proximal end 84 that is exposed to protrude from the corresponding saddle point 42 or 62. Each proximal end 84 has threads 86 that enable threaded attachment of the corresponding castle nut 78.

The remainder of the apparatus 70 is secured to the saddle points 42, 62 via the castle nuts 78. The bridge 72 spans the distance between the saddle points 42, 62 in a manner that enables relative cephalad/caudal motion with resilient support. The stabilization rod 74 is movably secured within the bridge 72 via the pins 76 to limit relative motion between the saddle points 42, 62 along the anterior direction 16, the posterior direction 18, and the medial/lateral axis 20. These functions and relationships will be described in greater detail in the discussion of FIG. 2, as follows.

Figure 2:
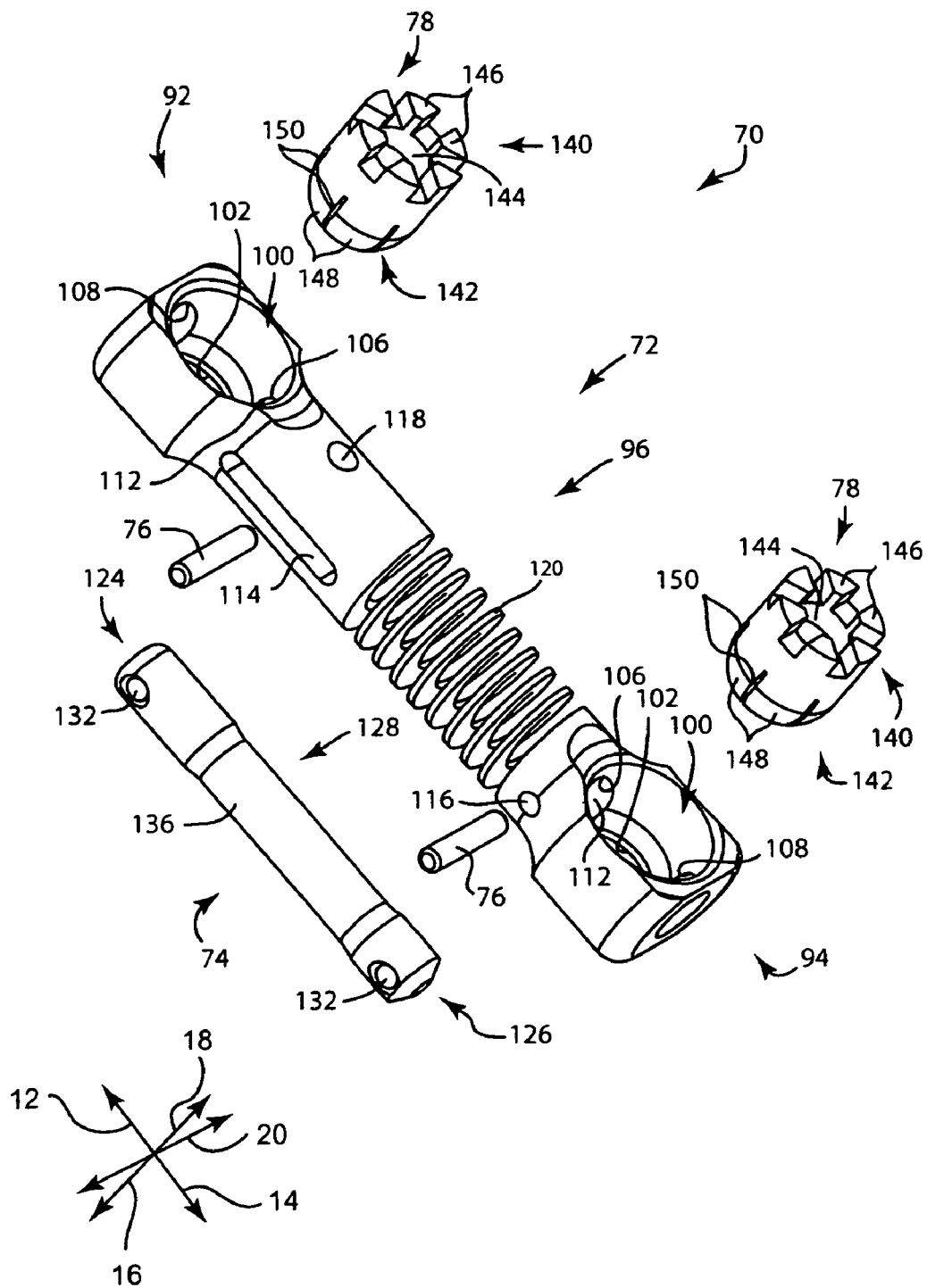
FIG. 2 is an exploded, perspective view of the apparatus of FIG. 1.

Referring to FIG. 2, an exploded, perspective view illustrates one of the apparatus 70 of FIG. 1 in isolation. As shown, the bridge 72 has a first end 92, a second end 94, and a central portion 96 between the first and second ends 92, 94. The first end 92 may be coupled to the first vertebra 24, and the second end 94 may be coupled to the second vertebra 26, so that upon implantation, the first end 92 is generally cephalad and the second end 94 is generally caudal.

Each of the first and second ends 92, 94 has a mounting interface 100 that facilitates attachment of the first or second end 92 or 94 to the corresponding saddle point 42 or 62. Each of the first and second ends 92, 94 also has a mounting aperture 102 from which the corresponding mounting interface 100 extends. The mounting interfaces 100 and the mounting apertures 102 may each be sized to permit passage of the corresponding proximal end 84 therethrough. Moreover, the mounting interfaces 100 and mounting apertures 102 are sufficiently large that the proximal end 84 may pass therethrough at a variety of angles nonparallel to the axis of the mounting interface 100 and mounting aperture 102. Thus, the apparatus 70 accommodates spinal morphologies in which the pedicles 30, 50 are not perpendicular to the desired orientation of the bridge 72 by permitting the fixation members 80 to extend non-perpendicular to the bridge 72.

Each mounting interface 100 has a generally concave, semispherical shape that is designed to receive and compress the corresponding castle nut 78 to substantially prevent relative rotation between the bridge 72 and the corresponding fixation member 80. Therefore, the orientation of the bridge 72 with respect to the fixation members 80 may be fixed in any of a variety of orientations to accommodate differing spinal morphologies. The manner in which the castle nuts 78 cooperate with the mounting interfaces 100 will be described in greater detail subsequently.

As shown, each of the mounting interfaces 100 has an interior orifice 106 and an exterior orifice 108. The interior orifices 106 provide communication with a bore 112 of the central portion 96 of the bridge 112, and the exterior orifices 108 provide access to the interior orifices 106. Thus, the stabilization rod 74 may easily be installed in the bore 112 by inserting the stabilization rod 74 through one of the exterior orifices 108, and then through the adjacent interior orifice 106.

The central portion 96 has a pin registration slot 114 adjacent to the first end 92, and a pin registration orifice 116 adjacent to the second end 94. The pin registration slot 114 and the pin registration orifice 116 communicate with the bore 112, and are designed to receive the pins 76. More precisely, the pin registration orifice 116 receives the corresponding pin 76 such that the pin 76 is unable to move with respect to the bridge 72 along the cephalad, caudal, anterior, and posterior directions 12, 14, 16, 18. The pin registration slot 118 receives the other pin 76 such that the pin 76 is unable to move with respect to the bridge 72 along the anterior and posterior directions 16, 18, but may move along the pin registration slot 118 in the cephalad and caudal directions 12, 14.

In addition to the pin registration slot 114 and the pin registration orifice 116, the central portion 96 has a supplemental orifice 118, which may be used to carry out various functions. According to one example, a set screw (not shown in FIG. 1) or other implement may be seated in the supplemental orifice 118 to restrict sliding of the stabilization rod 74 within the bore 112, thereby converting the apparatus 70 from a stabilization device to a fixation, or fusion device.

The central portion 96 also has a resilient section 120, which may take the form of a linear spring integrally formed with the remainder of the bridge 72. The resilient section 120 permits the first and second ends 92, 94 to move toward or away from each other to enable relative cephalad/caudal motion of the saddle points 42, 62 of the vertebrae 24, 26, respectively. The resilient section 120 also provides resilient force tending to push or pull the ends 92, 94 into a relative position in which the resilient section 120 is substantially undeflected. Such a position may correspond to a spinal disposition in which the vertebrae 24, 26 are neither flexed nor extended with respect to each other.

In FIG. 2, the resilient section 120 is integrally formed with the first and second ends 92, 94 of the bridge 72. In alternative embodiments (not shown), a resilient section may be separately formed from ends to which the resilient section is permanently or removably attached. For example, if the resilient section 120 were a separate piece from the ends 92, 94, the stabilization rod 74 would act to hold the resilient section 120 and the ends 92, 94 together after the bridge 72 and the stabilization rod 74 had been assembled.

Returning to the embodiment of FIG. 2, the stabilization rod 74 has a first end 124, a second end 126, and a central portion 128 between the first and second ends 124, 126. Each of the first and second ends 124, 126 has a pin registration orifice 132 sized to receive the corresponding pin 76. More specifically, the pin registration orifices 132 may be sized to receive the pins 76, with some interference to provide a press fit so that, once inserted into the orifices 132, the pins 76 remain in place until deliberately removed.

The ends 124, 126 may each be sized to fit into the bore 112 of the bridge 72 with relatively little clearance to maintain coaxiality between the bridge 72 and the stabilization rod 74. Alternatively, if desired, coaxiality may be maintained by providing relatively small clearance between the pins 76 and the pin registration slot 114 and the pin registration orifice 116. Maintaining coaxiality between the bridge 72 and the stabilization rod 74 restricts relative motion of the first and second ends 92, 94 of the bridge 72 to motion along the axis of the bridge 72, thereby permitting significant relative motion between the saddle points 42, 62 only along the cephalad and caudal directions 12, 14.

The central portion 128 has a stepped down region 136 with a diameter slightly smaller than that of the first and second ends 124, 126. Thus, clearance exists between the stepped down region 136 and the inward-facing surfaces of the resilient section 120 so that the resilient section 120 will not bind on the central portion 128 as the ends 92, 94 of the bridge 72 move together or apart.

Each of the castle nuts 78 has a torquing end 140 and a compression end 142. The torquing end 140 is designed to receive torque from a tool (not shown) with an end that meshes with the torquing end 140. The compression end 142 has a generally semispherical shape and is compressible to lock the orientation of the castle nut 78 with respect to the corresponding mounting interface 100. This permits locking of the orientation of the bridge 72 with respect to the fixation members 80 to prevent shear slippage of the vertebrae 24, 26 with respect to each other and to generally restrict relative anterior/posterior and medial/lateral motion between the vertebrae 24, 26.

Each castle nut 78 also has a bore 144 that passes through the torquing end 140 and the compression end 142. The bore 144 has threads (not shown) that mate with the threads 86 of the corresponding fixation member 80. The torquing end 140 has a plurality of crenellations 146 that enable the torquing tool (not shown) to interlock with the torquing end 140 without interfering with positioning of the proximal end 84 of the fixation member 80 in the bore 144.

The compression end 142 of each castle nut 78 has a plurality of fingers 148 arrayed in radially symmetrical fashion about the axis of the castle nut 78. The fingers 148 are separated from each other by slots 150 so that the fingers 148 are able to deflect inward upon engagement with the corresponding mounting interface 100. The fingers 148 are deflected inward in response to tightening of the castle nut 78 into the mounting interface 100 as the castle nut 78 is rotated to advance it along the proximal end 84 of the corresponding fixation member 80.

Deflection of the fingers 148 increases the contacting surface area between the compression end 142 and the mounting interface, thereby enhancing frictional engagement of the castle nut 78 with the mounting interface 100. The resulting frictional forces are generally adequate to maintain the relative orientations of the bridge 72 and the fixation members 80 during normal motion of the spine 10. The mating semi-spherical shapes of the compression ends 142 and the mounting interfaces 100 allow such frictional locking to occur in any of a variety of orientations of the bridge 72 with respect to the fixation members 80, thereby permitting usage of the apparatus 70 with a variety of spinal morphologies.

Figure 3:
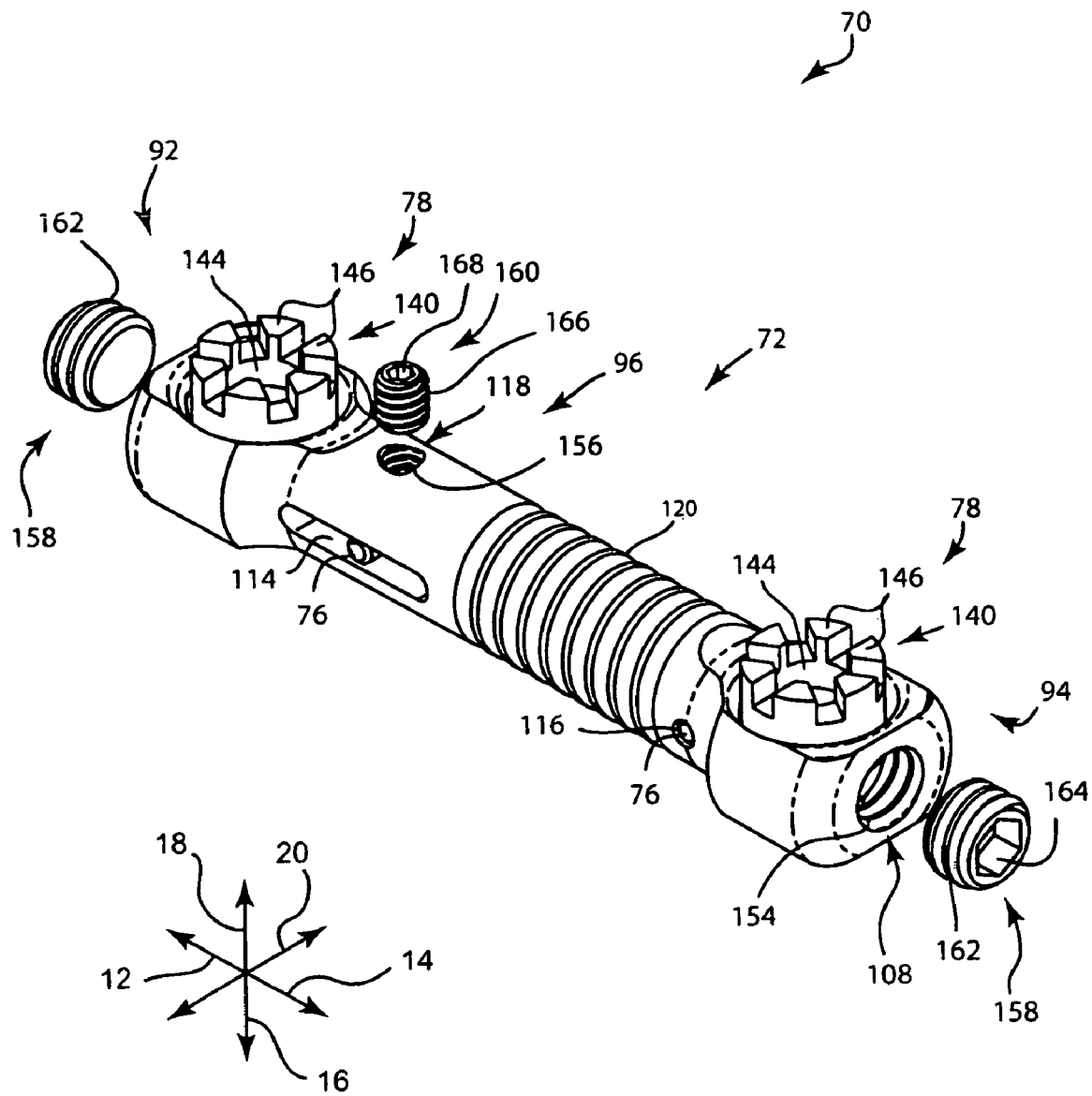
FIG. 3 is a partially exploded, perspective view illustrating the apparatus of FIG. 1 with optional components including end caps and a set screw.

Referring to FIG. 3, a partially exploded view illustrates the apparatus 70 of FIGS. 1 and 2, with extra components to help lock the apparatus 70 to substantially prevent elongation, contraction, and/or rotation of the apparatus 70. As shown, each of the exterior orifices 108 may have a plurality of threads 154. Similarly, the supplemental orifice 118 may have a plurality of threads 156. The extra components, shown exploded from the apparatus 70 in FIG. 3, include a pair of end plugs 158 that may be received by the exterior orifices 108, and a locking component, which may take the form of a set screw 160, which may be received by the supplemental orifice 118.

As shown, each of the end plugs 158 has threads 162 designed to interface with the threads 154 of the corresponding exterior orifice 108. Furthermore, each of the end plugs 158 has a torquing feature 164, such as a hexagonal recess, that facilitates rotation of the end plug 158 through the use of a suitable too such as a hex-head driver. Thus, each end plug 158 can be rotated into engagement with the corresponding exterior orifice 108.

Similarly, the set screw 160 has threads 166 that interface with the threads 156 of the supplemental orifice 118. The set screw 160 also has a torquing feature 168, such as a hexagonal recess, that operates in a manner similar to that of the torquing features 164 of the end plugs 158 to facilitate rotation of the set screw 160 into engagement with the supplemental orifice 118.

Figure 4:
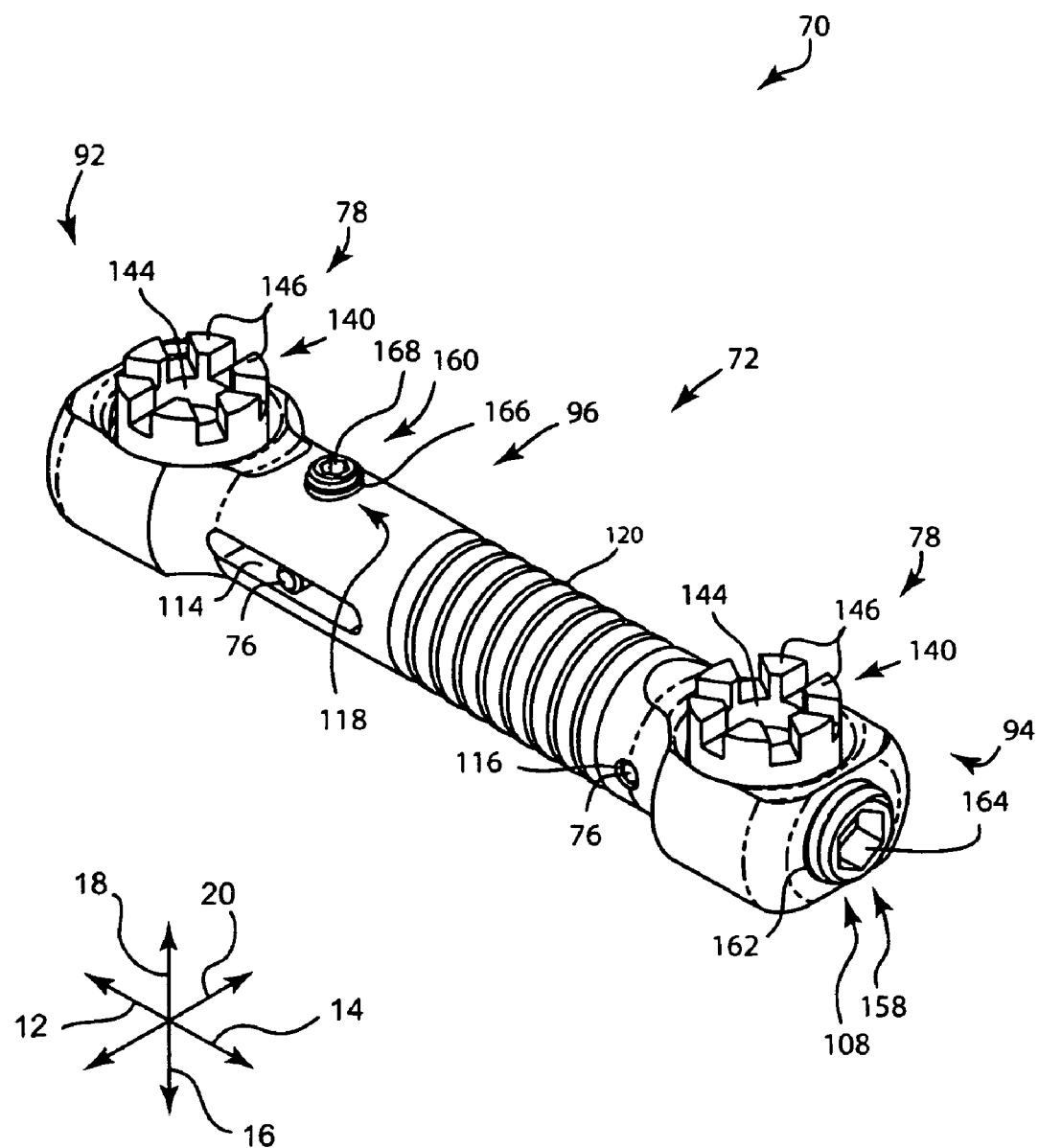
FIG. 4 is a perspective view of the apparatus of FIG. 1, with the end caps and set screw in place.

Referring to FIG. 4, a perspective view illustrates the apparatus 70 in fully assembled form, with the end plugs 158 and the set screw 160 in place. The end plugs 158 may be sufficiently actuated to cause the leading end of each end plug 158 to press against the side of the corresponding castle nut 78. Pressure against the castle nut 78 further restricts rotation of the castle nut 78 within the corresponding mounting interface 100, thereby further securing the ends 92, 94 against rotation with respect to the corresponding pedicles 30, 50. This tends to restrict flexion, extension, lateral bending, and axial rotation of the vertebrae 24, 26.

Although the ends 92, 94 are substantially secured against rotation with respect to the pedicles 30, 50 via engagement of the castle nuts 78 with the mounting interfaces 100, usage of the end plugs 158 provides additional securement. In alternative embodiments, the ends of a stabilizer may be allowed to dynamically rotate polyaxially with respect to vertebral attachment points. The apparatus 70 may easily modified to provide such polyaxiality. End plugs 158 may then be used to selectively restrict relative polyaxial motion.

The set screw 160 may be sufficiently actuated to cause the leading end of the set screw 106 to press against the first end 124 of the stabilization rod 74. Pressure against the first end 124 tends to arrest sliding of the first end 124 with respect to the first end 92 of the bridge 72, thereby keeping the apparatus 70 from elongating or contracting.

When the apparatus 70 is unable to elongate or contract, the vertebrae 24, 26 are substantially unable to move relative to each other in flexion, extension, lateral bending, and axial rotation. Accordingly, usage of the set screw 160, with or without the end plugs 158, may amount to fusion of the vertebrae 24, 26. If stabilization via the apparatus 70 is unsuccessful in preventing further damage to the intervertebral disc 66 or to the vertebrae 24, 26, the set screw 160 may easily be applied to fuse the vertebrae 24, 26 without requiring removal of the apparatus 70 or further removal of bone tissue.

It may be desirable to provide some structure to limit the ability of the vertebrae 24, 26 to move in axial rotation and/or lateral bending, without significantly limiting flexion or extension. This may be particularly desirable for a stabilizer with end points that are attached to the vertebrae in such a manner that polyaxial rotation between the end points and the vertebrae is permitted. Such polyaxial rotation may permit a pair of stabilizers to "windshield wiper," or rotate in tandem to permit relatively unrestricted axial rotation. Similarly, relative rotation of stabilizers of a bilateral pair may enable lateral bending.

Figure 5:
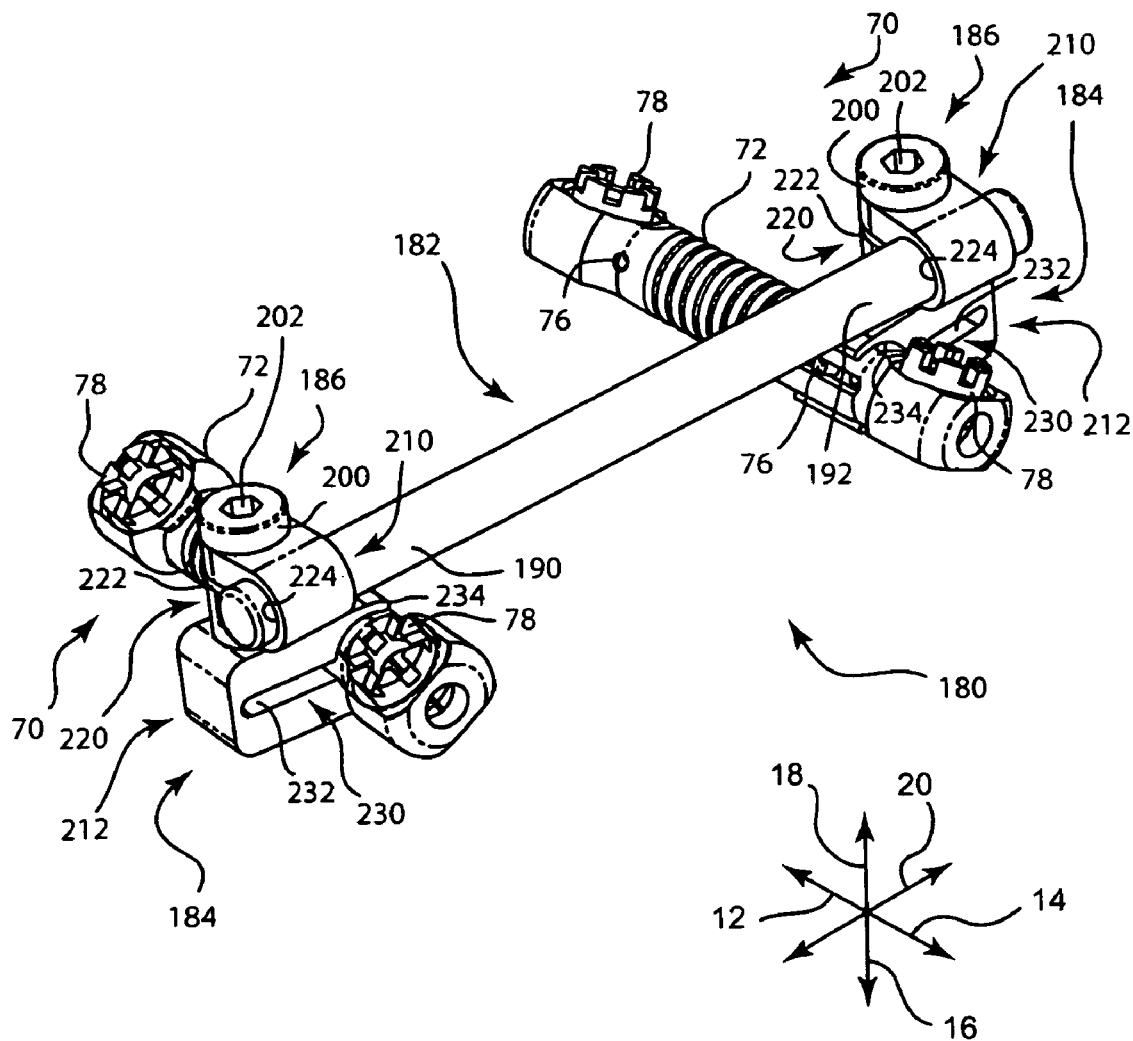
FIG. 5 is a perspective view of the left and right apparatus of FIG. 1, with a crosslink used to limit relative rotation of the left and right apparatus.

Referring to FIG. 5, a perspective view illustrates left and right apparatus 70 that are linked together via a crosslink 180. The crosslink 180 may operate to restrict relative rotation between the apparatus 70 on the left-hand side and the apparatus 70 on the right-hand side, thereby restricting relative axial rotation and/or lateral bending of a pair of vertebrae, as described above.

As shown, the crosslink 180 includes a rod 182, a pair of brackets 184, and a pair of fasteners, which may take the form of screws 186, that hold the brackets 184 to the rod 182 and the left and right apparatus 70. The rod 182 may have a generally cylindrical shape, and may pass generally underneath the spinous process 36 of the first vertebra 24 (shown in FIG. 1). The rod 182 has a first end 190 attached to one of the apparatus 70 and a second end 192 attached to the other apparatus 70.

Each screw 186 has a head 200, a shank (not shown), and a torquing feature 202 extending into the head. The torquing feature 202 may take the form of a hexagonal recess like those of the end plugs 158 and the set screw 160, as described previously. The shank may be threaded to interface with corresponding threads (not shown) of the brackets 184.

Each of the brackets 184 has a first grip 210 and a second grip 212. The first grip 210 is designed to secure each bracket 184 to the corresponding end 190, 192 of the rod 182. The second grip 212 secures each bracket 184 to the corresponding apparatus 70. The first and second grips 210, 212 are designed to be energized by the corresponding screw 186 to retain the rod 182 and the corresponding apparatus 70. For example, each of the brackets 184 may have a bore (not shown) extending through both of the grips 210, 212, with threads only on the end of the bore furthest from the end at which the corresponding head 200 will be positioned. Accordingly, tightening of each screw 186 may cause axial compression of the bore of the corresponding bracket 184.

The first grip 210 has a slot 220 with a compression portion 222 and a gripping portion 224. At the compression portion 222, the slot 220 is relatively narrow. At the gripping portion 224, the slot 220 widens to provide a generally cylindrical interior surface shaped to receive the corresponding end 190 or 192 of the rod 182. The sides of the compression portion 222 are drawn toward each other by tightening the corresponding screw 186. As a result, the sides of the gripping portion 224 press inward against the corresponding end 190 or 192 for secure retention.

The second grip 212 similarly has a slot 230 with a compression portion 232 and a gripping portion 234. At the compression portion 232, the slot 230 is relatively narrow. At the gripping portion 234, the slot 230 widens to provide a generally cylindrical interior surface shaped to receive the first end 92 of the bridge 72 of the corresponding apparatus 70. The sides of the compression portion 232 are drawn toward each other by tightening the corresponding screw 186. As a result, the sides of the gripping portion 234 press inward against the end 92 of the bridge 72 of the corresponding apparatus 70 for secure retention.

The brackets 184 enable efficient installation because tightening the screws 186 causes the brackets 184 to simultaneously retain the rod 182 and the left and right apparatus 70. According to one installation method, after the left and right apparatus 70 have been attached to the vertebrae 24, 26, the crosslink 180 can be easily inserted into loose engagement with the left and right apparatus 70, such that the rod 182 is not securely retained. With the vertebrae 24, 26 at the desired relative orientation in axial rotation and lateral bending (presumably a neutral orientation), the screws 186 can be tightened to restrict further relative rotation between the left and right apparatus 70, thereby restricting further axial rotation and/or lateral bending.

According to alternative embodiments, a crosslink need not extend between two stabilizers. For example, a crosslink (not shown) may have a first end attached to one apparatus 70, and a second end attached directly to one of the vertebrae 24, 26. The second end may be attached to any desirable feature such as a pedicle 30 or 50 or a spinous process 36 or 56. Such a crosslink would inhibit rotation of the apparatus 70 with respect to the vertebrae 24, 26 in a manner similar to that of the crosslink 180. Such a crosslink may be particularly desirable if only one stabilizer is used. An end of a crosslink that is "substantially secured" with respect to a vertebra may be attached to a stabilizer such as the apparatus 70 coupled to the vertebra, attached directly to the vertebra, or indirectly attached to the vertebra through the use of a different element such as a fastener or another type of spinal prosthesis.

Additionally, a wide variety of other crosslink embodiments may be used. For example, in place of the brackets 184, retention members (not shown) may be attached to the apparatus 70 or to the rod 182 via adhesives, set screws, clips, or other devices. Furthermore, if desired, a crosslink may be made from fewer pieces. For example, two telescoping rod segments may each have an integrated end capable of being attached to one apparatus 70. As another example, a crosslink may be designed to provide locking as well as crosslinking, thereby making it unnecessary to install a separate locking component. Such a crosslink may have a built-in set screw or other locking component, or may otherwise retain the corresponding stabilizers in such a manner that they are unable to elongate or contract when the crosslink is in place. Those of skill in the art will recognize that a wide range of alternatives may be used within the scope of the present invention.

Usage of the apparatus 70 may beneficially add stiffness in flexion, extension, axial rotation, and lateral bending, whether used with or without the crosslink 180. The crosslink 180 may help to add additional stiffness in axial rotation and lateral bending. The manner in which the apparatus 70 and/or the crosslink 180 may help to restore natural spinal biomechanics will be shown and described with reference to FIGS. 6 and 7, as follows.

Figure 6:
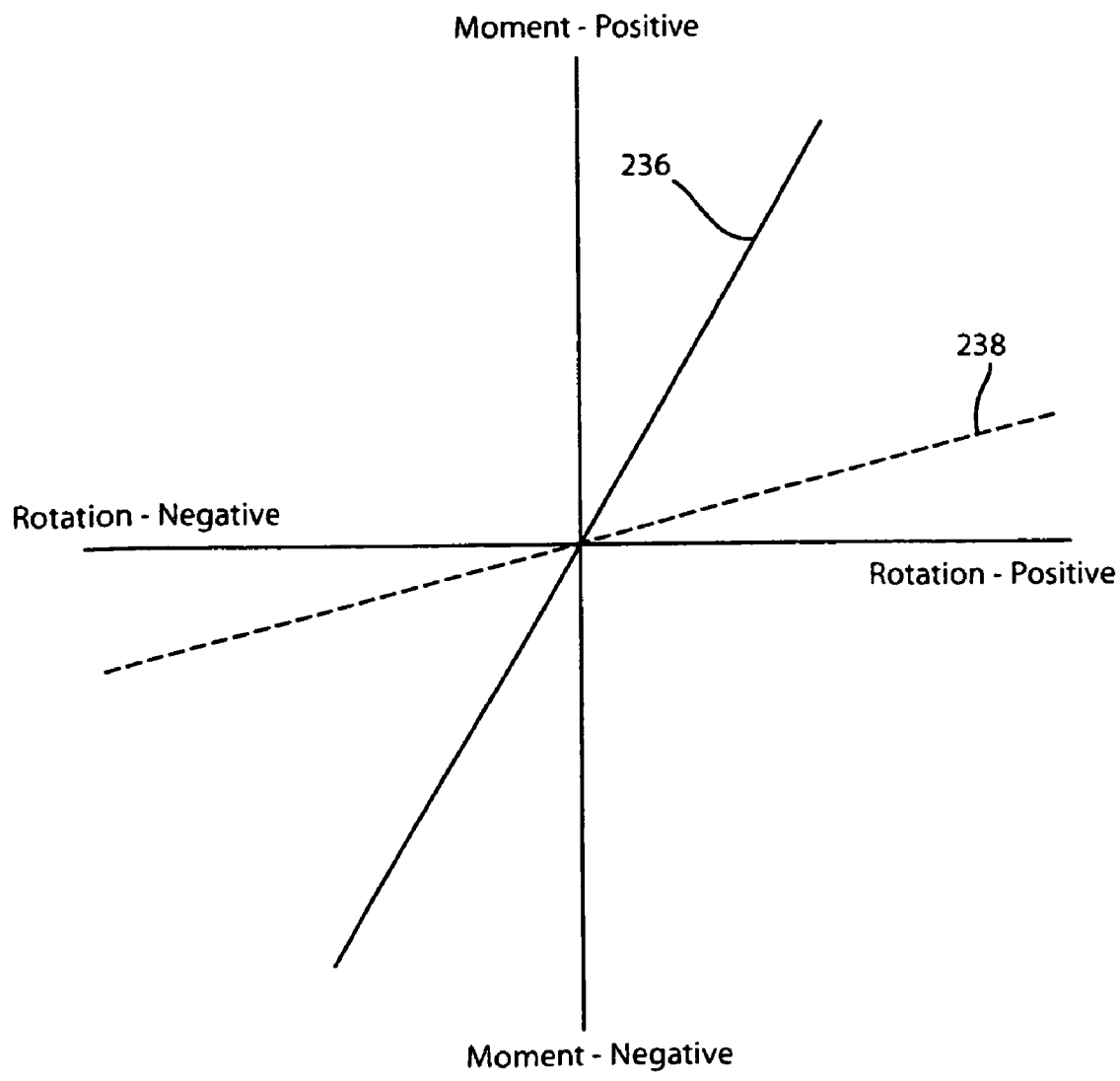
FIG. 6 is a chart illustrating corrected and pathological rotation/moment curves for typical prior art stabilization devices.

Referring to FIG. 6, a chart illustrates the manner in which the flexion, extension, axial rotation and/or lateral bending of a damaged or diseased joint motion segment may be adjusted according to many prior art methods. According to traditional thinking, a corrected displacement curve 236 shows the magnitude of flexion, extension, axial rotation, and/or lateral bending of two vertebrae separated by a healthy intervertebral disc as a function of moment loading. A pathological displacement curve 238 shows the magnitude of axial rotation or lateral bending of two vertebrae separated by a diseased or damaged intervertebral disc as a function of moment loading according to some traditional analysis methods.

When applied to a joint motion segment having the pathological displacement curve 238, a stabilizer adds stiffness in flexion, extension, axial rotation, and/or lateral bending across substantially the entire range of motion of the joint. Known stabilizers often have resilient members that provide a single spring constant across the entire range of motion, thereby applying a proportionate increase in stiffness along the range of motion of the joint. The result is to move a spinal motion segment from the motion characteristics of the pathological displacement curve 238 toward those of the corrected displacement curve 236. Since such a stabilizer may not provide any mechanical stops, the corrected displacement curve 236 has a substantially constant slope, which does not accurately replicate natural biomechanics.

Figure 7:
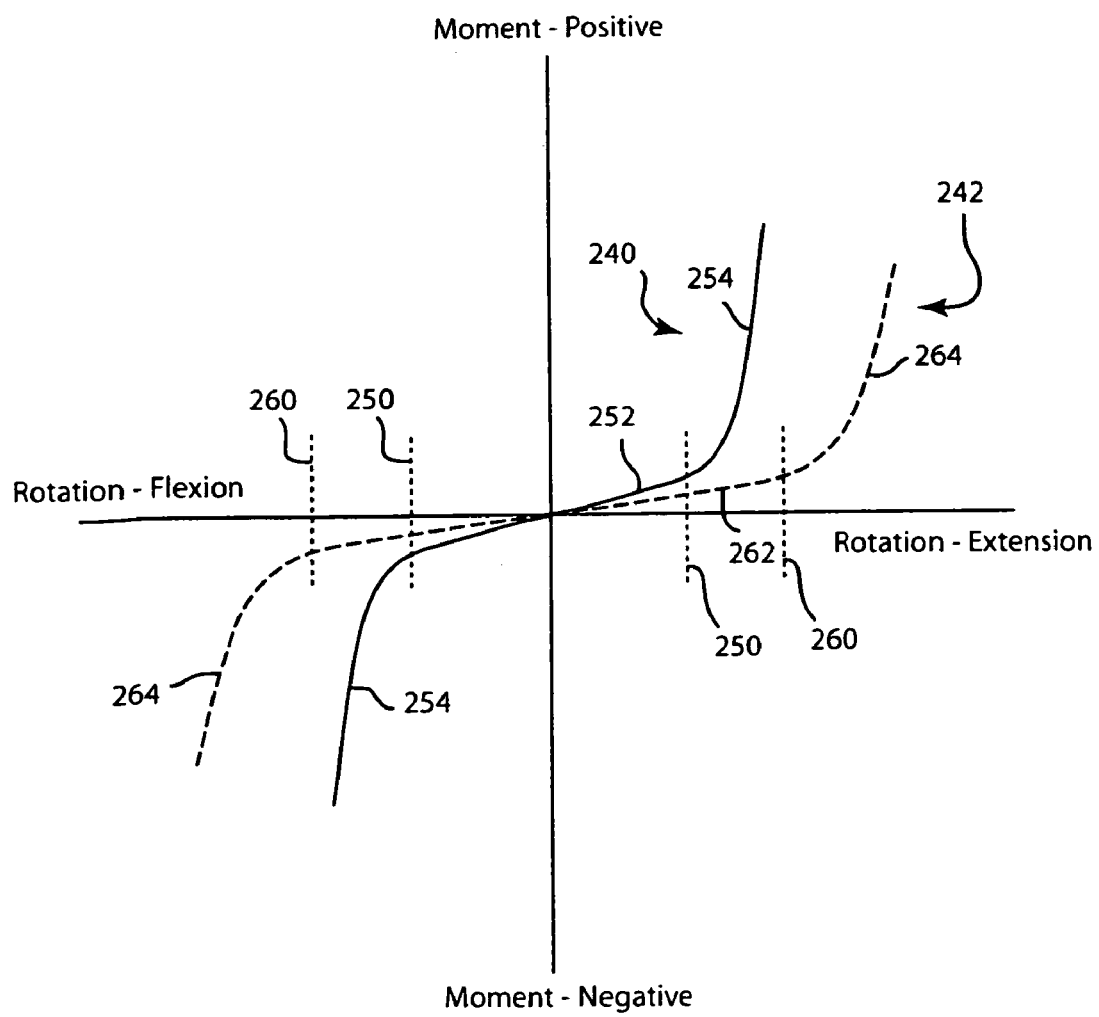
FIG. 7 is a chart illustrating natural (corrected) and pathological rotation/moment curves for the apparatus of FIG. 1.

Referring to FIG. 7, a chart illustrates the manner in which the flexion and extension of a damaged or diseased joint motion segment can be enhanced through the use of the apparatus 70, or any other stabilizer according to the invention. A natural displacement curve 240 shows the natural magnitude of relative rotation as a function of moment loading of two vertebrae separated by a healthy intervertebral disc, healthy facet joints, and connected by healthy ligaments. A pathological displacement curve 242 shows the magnitude of relative rotation as a function of moment loading of two vertebrae separated by one or more of: diseased or damaged intervertebral disc, diseased or damaged ligaments, and diseased or damaged facet joints. The natural displacement curve 240 also represents an ideal displacement curve after the application of the apparatus 70 to a pathological joint motion segment, where restoration of natural biomechanics has been achieved.

As shown, a pair of boundaries 250 illustrates the limits of a neutral zone 252 of the natural displacement curve 240. Within the neutral zone 252, relatively large displacement occurs because the stiffness of the intervertebral disc, ligaments, facet joint capsules and other adjacent tissues is relatively low. Outside the boundaries 250, the natural displacement curve 240 has motion limited zones 254 within which the stiffness of these members is greater due to the fact that they are under higher deflection. Additionally, within the motion limited zones 254, abutment of bone structures such as facet joints may contribute a relative larger stiffness so that relatively small displacement occurs with the incremental addition of moments.

Boundaries 260 similarly illustrate the limits of a neutral zone 262 of the pathological displacement curve 242. Outside the boundaries 260, the pathological displacement curve 242 has motion limited zones 264 within which motion in response to incremental addition of moments is generally more limited than within the neutral zone 262. Generally, the pathological displacement curve 242 exhibits far more motion for any given input moment than the natural displacement curve 240. The slope of the neutral zone 262 is lower than that of the neutral zone 252, and the boundaries 260 are not reached until a higher moment is applied. The slopes of the motion limited zones 264 may even be higher than those of the motion limited zones 254. As mentioned previously, such a condition may accelerate deterioration of, and necessary surgical intervention for, the intervertebral disc due to excessive intervertebral motion.

When applied to a joint motion segment having the pathological displacement curve 242, the apparatus 70 of FIGS. 1 through 5 beneficially adds stiffness in flexion and extension across substantially the entire range of motion of the joint. When the crosslink 180 is also in place, even more stiffness in axial rotation and lateral bending may be added, without significantly inhibiting motion in flexion and extension. The result is to move a spinal motion segment from the motion characteristics of the pathological displacement curve 242 back toward those of the natural displacement curve 240. It may be desirable to stiffen the spinal motion segment even beyond the level of stiffness provided by a natural, healthy spinal motion segment to protect a diseased or damaged intervertebral disc from further damage.

More precisely, the resilient section 120 of the central portion 96 of the bridge 72 adds stiffness that increases the slope of the neutral zone 262 to approximate that of the neutral zone 252 of the natural displacement curve 240. The boundaries 260 are thus brought inward proximate the locations of the boundaries 250. Within the motion limited zones 264 of the pathological displacement curve 242, the apparatus 70 provides mechanical stops that limit motion by providing additional stiffness to approximate the motion limited zones 254 of the natural displacement curve 240. Such mechanical stops may include, but are not limited to, the ends of the pin registration slot 114 of the central portion 96 of the bridge 72 because the ends of the pin registration slot 114 limit extension and contraction of the apparatus 70.

It has been discovered that the natural and pathological displacement curves 240, 242 of FIG. 7 more accurately characterize the stiffness of a joint than the corrected and pathological displacement curves 236, 238 of FIG. 6. The present invention is more closely tuned to correcting the actual pathology, and to providing a displacement curve that more closely approximates the natural displacement curve of a joint.

The apparatus 70 of FIGS. 1 through 5 is only one of many different designs that can provide dynamic stabilization according to the invention. The apparatus 70 utilizes stabilization, as provided by the stabilization rod 74, in conjunction with a resilient member, i.e., the resilient section 120 of the central portion 96 of the bridge 72, to provide motion characteristics that provide the needed stabilization while more closely replicating natural kinematics. In the apparatus 70, the stabilization rod 74 passes through the resilient section 120. However, in selected alternative embodiments, a stabilization assembly may extend around the outside of a resilient member. Such an embodiment will be shown and described in connection with FIGS. 8 through 10, as follows.

Figure 8:
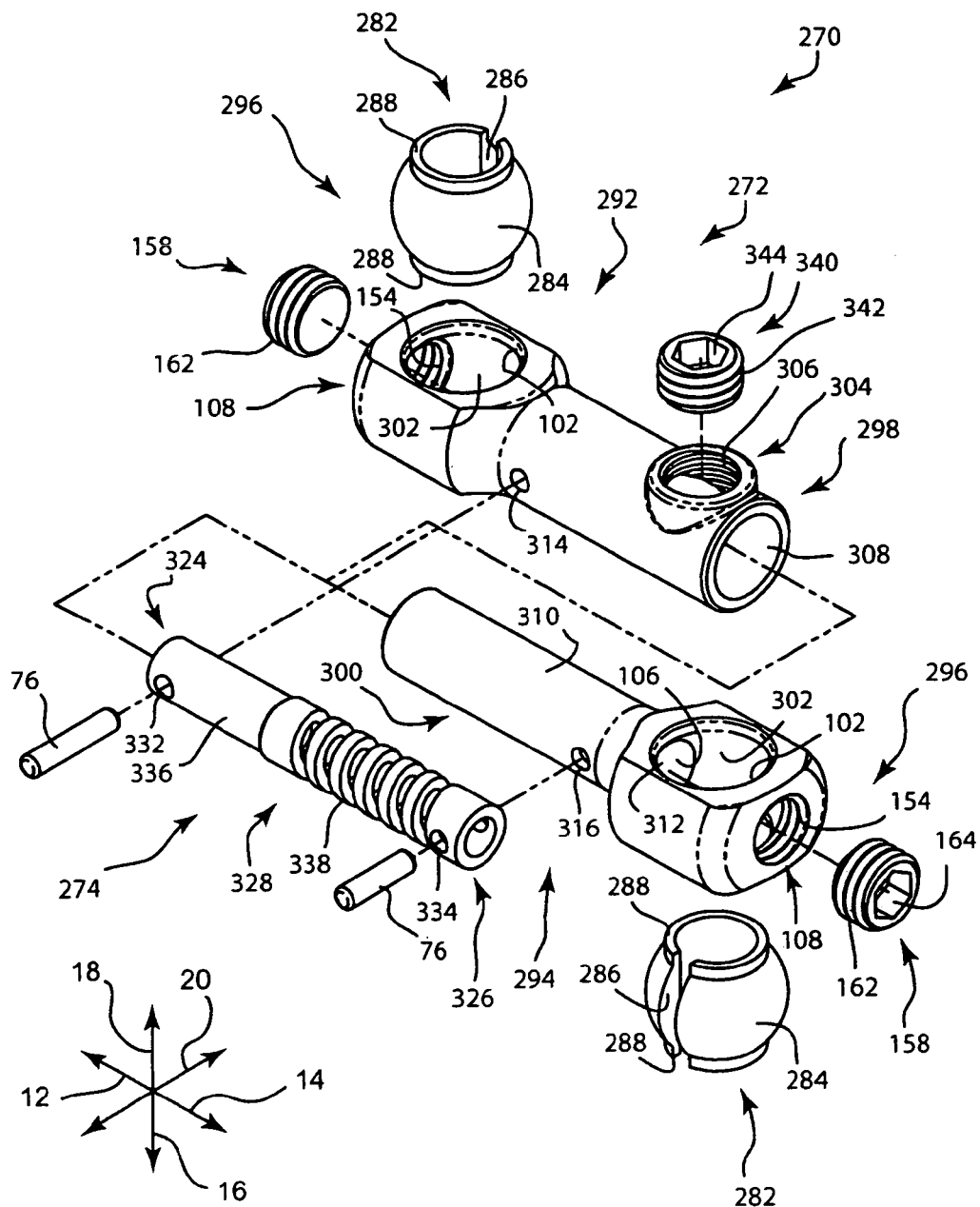
FIG. 8 is an exploded, perspective view illustrating an apparatus according to one alternative embodiment of the invention.

Referring to FIG. 8, an exploded, perspective view illustrates an apparatus 270 according to one alternative embodiment of the invention. The apparatus 270 includes castle nuts (not shown), each of which has a threaded bore and a torquing interface such as the crenellations 146 of the castle nuts 78 of the previous embodiment. However, the castle nuts of the current embodiment do not have a compression end because they are not designed to lock the apparatus 270 to prevent rotation with respect to the vertebrae 24, 26 (shown in FIG. 1). Rather, the castle nuts have flat ends that hold the ends of the apparatus 270 against the pedicles 30, 50, while permitting limited polyaxial relative rotation due to the structure of the ends of the apparatus 270, as will be described subsequently. The castle nuts may cooperate with fixation members 80 like those of the previous embodiment to attach the apparatus 270 to the vertebrae 24, 26.

In addition to the castle nuts and fixation members 80, the apparatus 270 includes a bridge 272, a resilient rod 274, a pair of pins 76, and a pair of split spheres 282. The bridge 272 does not provide resiliency, but rather, acts as a stabilization assembly. The resilient rod 274 provides resiliency. Thus, the bridge 272 and the rod 274 cooperate to perform a function similar to that of the bridge 72 and the stabilization rod 74 of the previous embodiment. The pins 76 may be identical to those of the previous embodiment.

Each of the split spheres 282 may be formed of a relatively pliable material such as a polymer. Each split sphere 282 may have a semispherical surface 284 with an open portion 286 that permits the split sphere 282 to flex to enlarge or contract the semispherical surface 284. Furthermore, each split sphere 282 has a pair of end rings 288. Each end ring 288 has a generally tubular configuration that protrudes beyond the adjacent semispherical surface 284. The split spheres 282 operate to enable polyaxial rotation of the apparatus 270 with respect to the vertebrae 24, 26 in a manner that will be described subsequently. The polyaxial rotation is "dynamic," which means that it is able to occur after the apparatus 270 has been securely attached to the pedicles 30, 50.

As shown, the bridge 272 of FIG. 3 has a first containment member 292 and a second containment member 294. The containment members 292, 294 cooperate to substantially contain the resilient rod 274, as will be described in greater detail subsequently. Each of the first and second containment members 292, 294 has an end 296. Additionally, the first containment member 292 has a telescoping portion 298, and the second containment member 294 has a telescoping member 300 designed to telescopically engage the telescoping portion 298 of the first containment member 292.

Each end 296 has a mounting interface 302 with a generally semispherical shape that converges to a pair of generally symmetrical mounting apertures 102, only one of which is visible on each mounting interface 302 in FIG. 8. Like the mounting interface 100 of the previous embodiment, each mounting interface 302 has an interior orifice 106 and an exterior orifice 108. The interior and exterior orifices 106, 108 cooperate to facilitate installation of the resilient rod 274 within the bridge 272. Furthermore, the exterior orifices 108 may receive end plugs 158 like those of the previous embodiment to facilitate locking of the apparatus 270 to optionally prevent rotation with respect to the vertebrae 24, 26 after attachment. Additionally, the telescoping portion 298 of the first containment member 292 has a supplemental orifice 304 with threads 306 to facilitate locking, as will be discussed subsequently.

The first telescoping portion 298 has an interior surface 308 with a generally cylindrical shape. The second telescoping portion 300 is designed to slide within the first telescoping portion 298, and therefore has an exterior surface 310 that fits within the interior surface 308 with clearance. The second telescoping portion 300 also has an interior surface 312 within which the resilient rod 274 is generally positionable.

The first containment member 292 has a pin registration orifice 314 positioned generally at the juncture of the corresponding end 296 with the telescoping portion 298. The pin registration orifice 314 is sized to receive the corresponding pin 76 with either clearance or interference, as desired. The second containment member 294 similarly has a pin registration orifice 316 positioned generally at the juncture of the corresponding end 296 with the telescoping portion 300 to receive the corresponding pin 76 with either clearance or interference. The telescoping portion 300 of the second containment member 294 has a stepped down interior surface (not visible in FIG. 8) that is sized to fit with relatively small clearance around the corresponding portion of the resilient rod 274.

The resilient rod 274 has a first end 324, a second end 326, and a central portion 328 between the first and second ends 324, 326. The first end 324 has a pin registration orifice 332 designed to receive the corresponding pin 76 in concert with the pin registration orifice 314 of the first containment member 292. Similarly, the second end 326 has a pin registration orifice 334 designed to receive the corresponding pin 76 in concert with the pin registration interface 316 of the second containment member 294.

The central portion 328 has a stepped down region 336 designed to reside within the stepped down interior surface 350 of the telescoping portion 300 of the second containment member 294. The stepped down region 336 may fit into the stepped down interior surface 350 with relatively small clearance so that the engagement of the stepped down region 336 with the stepped down interior surface (not visible in FIG. 8) helps to maintain coaxiality of the bridge 272 with the resilient rod 274. The central portion 328 also has a resilient section 338, which may be a linear spring like that of the resilient section 120 of the previous embodiment.

As in the previous embodiment, the resilient section 338 is integrally formed with the remainder of the resilient rod 274. However, in alternative embodiments (not shown), a resilient section may be a separate piece with the remainder of a resilient rod, and may be attached to the other resilient rod components or may remain coupled thereto by virtue of assembly with the corresponding bridge.

Returning to the apparatus 270 of FIG. 3, a locking component may optionally be provided. The locking component may take the form of a set screw 340 configured somewhat similarly to the set screw 160 of the previous embodiment, in that the set screw 340 has threads 342 and a torquing feature 344. The threads 342 are shaped to mate with the threads 306 of the supplemental orifice 304 so that the set screw 340 can be rotated into engagement with the supplemental orifice 304.

Figure 9:
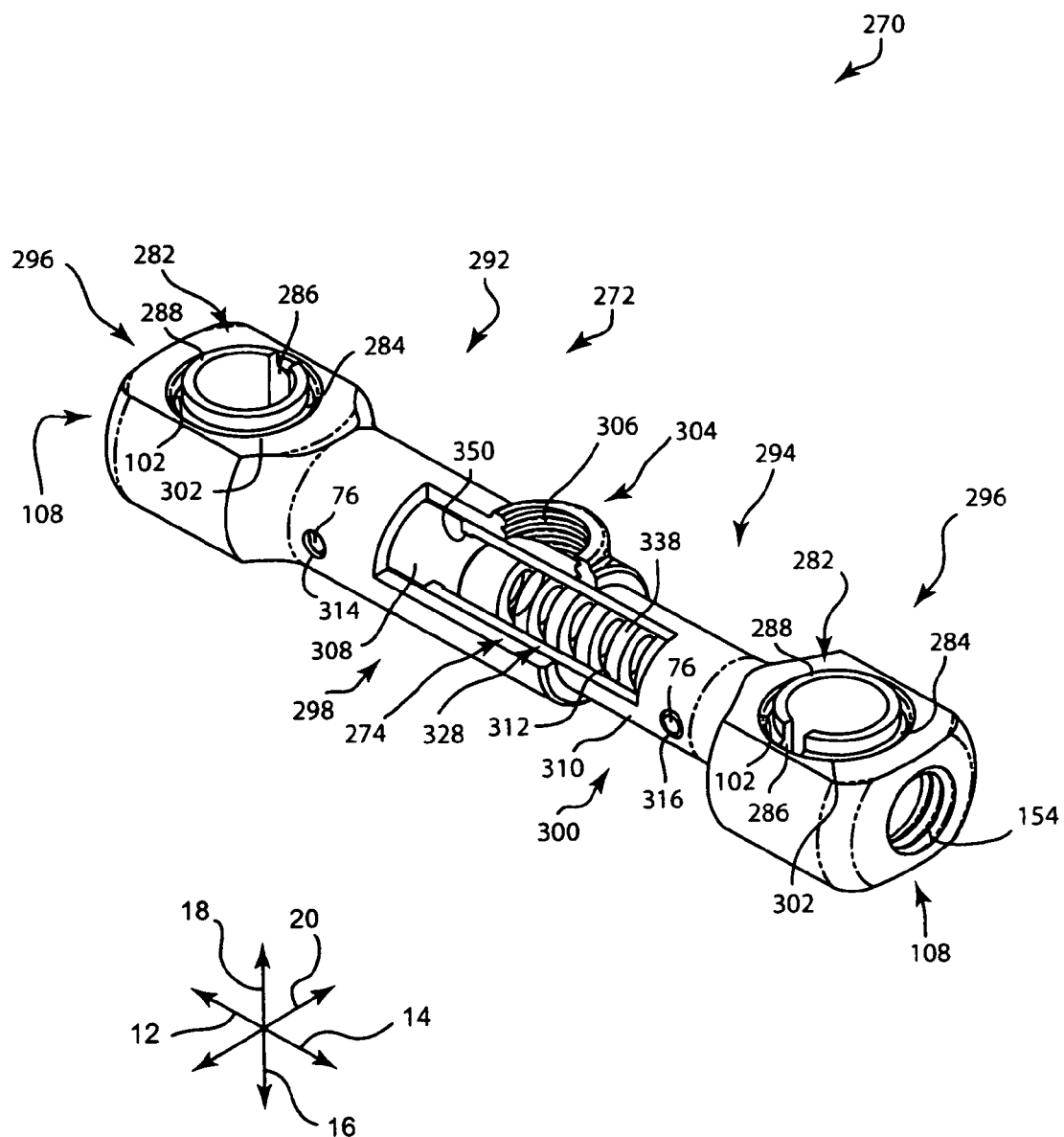
FIG. 9 is a perspective, partially cutaway view of the apparatus of FIG. 8.

Referring to FIG. 9, a fully assembled, partially cut away view illustrates the apparatus 270 in a fully assembled state, without the end plugs 158 and the set screw 340. As described previously, the telescoping portion 300 of the second containment member 294 has a stepped down interior surface 350 that fits around the stepped down region 336 of the central portion 328 of the resilient rod 274 with relatively little clearance. The stepped down interior surface 350 may slide relatively freely around the stepped down region 336, but the clearance between the two may be small enough to inhibit relative rotation between the containment members 292, 294, except about the axis of the containment members 292, 294. The split spheres 282 have been inserted into the corresponding mounting interfaces 302.

The bridge 272 and the resilient rod 274 may be relatively easily assembled by sliding the stepped down region 336 of the resilient rod 274 through the exterior orifice 108, the interior orifice 106, and then into the stepped down interior surface 350 of the second containment member 294. The second end 326 of the resilient rod 274 may be fixed with respect to the end 296 of the second containment member 294 by sliding one of the pins 76 through the pin registration orifice 316 of the second containment member 294, and through the pin registration orifice 334 of the second end 326 of the resilient rod. The first end 324 of the resilient rod 274 may then be fixed with respect to the end 296 of the first containment member 292 by sliding the other pin 76 through the pin registration orifice 314 of the first containment member 292, and through the pin registration orifice 332 of the first end 324 of the resilient rod.

By virtue of the pins 76, the engagement of the interior surface 308 with the exterior surface 310, and/or the engagement of the stepped down region 336 with the stepped down interior surface 350, the first and second containment members 292, 294 may be constrained to remain substantially coaxial with each other and with the resilient rod 274. The resilient section 338 provides resilient force to urge the saddle points 42, 62 to a displacement in which the resilient section 338 is substantially undeflected. Thus, the apparatus 270 performs a function similar to that of the apparatus 70 of FIG. 1. In alternative embodiments, an apparatus like the apparatus 270 may be tuned to provide slight distraction of the vertebrae 24, 26, i.e., urge the posterior elements of the vertebrae 24, 26 to move apart from each other more than in a normal neutral position of the spinal motion segment to further protect the intervertebral disc 66 from damage.

Figure 10:
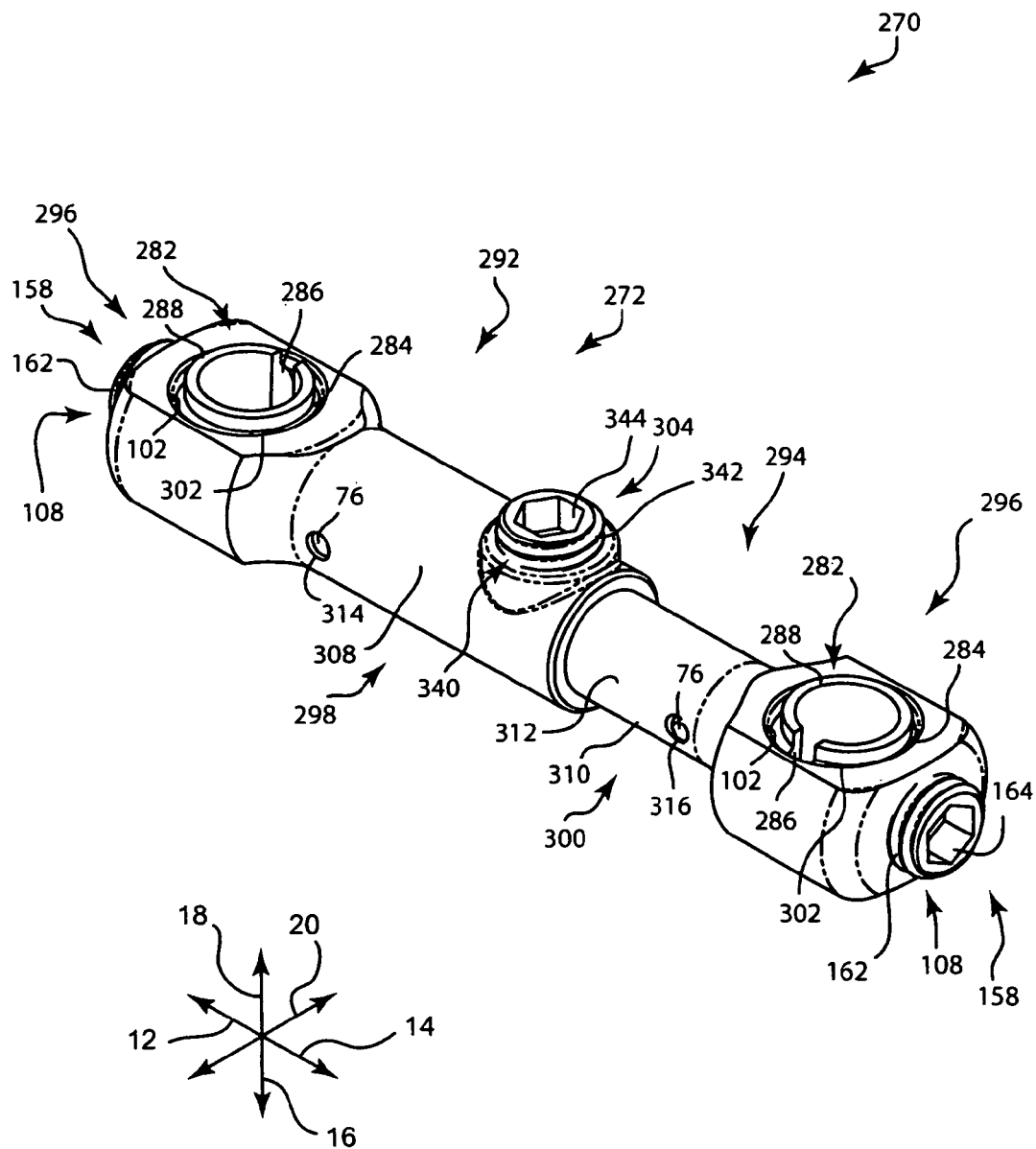
FIG. 10 is a perspective view of the apparatus of FIG. 8, with end caps and a set screw in place.

Referring to FIG. 10, a perspective view illustrates the apparatus 270 in a fully assembled state, with the end plugs 158 and the set screw 340 in place. Prior to installation of the end plugs 158, the ends 296 of the containment members 292, 294 are able to rotate polyaxially with respect to the corresponding saddle points 42, 62. The proximal ends 84 of the fixation members 80 (shown in FIG. 1) pass through the split spheres 282, and the castle nuts (not shown) are rotated into place to press against the exposed end rings 288 of the split spheres 282 to hold the split spheres 282 relatively securely to the fixation members 80.

The semispherical surfaces 284 of the split spheres 282 articulate with the mounting interfaces 302 to permit triaxial rotation of each end 296 relative to the fixation member 80 that passes through it. Each of the end rings 288 may serve as a motion stop by contacting the adjacent mounting aperture 102 of the corresponding mounting interface 302 when the end 296 reaches a pre-established orientation with respect to the corresponding vertebra 24 or 26. If desired, alternative embodiments (not shown) may utilize end rings with non-circular peripheries to provide tighter control over the polyaxiality provided by the corresponding split sphere. For example, an oval-shaped, squared, or otherwise deliberately shaped end ring may be used as a cam to permit a higher degree of rotation about one axis than about another.

The end plugs 158 are rotated into the exterior orifices 108 to abut against the split spheres 282, thereby restricting, or even preventing, rotation of the ends 296 relative to the vertebrae 24, 26. More precisely, end interior ends of the end plugs 158 engage the semispherical surfaces 284 of the split spheres 282, thereby restricting rotation of the split spheres 282 within the mounting interfaces 302. Thus, the apparatus 270 is then constrained to remain at a fixed orientation with respect to the vertebrae 24, 26.

As the set screw 340 is tightened into abutment with the exterior surface 310 of the telescoping portion 300 of the second containment member 294, pressure of the set screw 340 against the exterior surface 310 prevents further relative motion between the telescoping portions 298, 300. Thus, the apparatus 270 is unable to elongate or contract, and as with usage of the set screw 160 of the previous embodiment, flexion, extension axial rotation, and lateral bending are substantially prevented. As in the previous embodiments, the set screw 340 and the end plugs 158 may cooperate to lock the apparatus 270 to substantially fuse the vertebrae 24, 26 together. However, as in the previous embodiment, the set screw 340 and the end plugs 158 may be used independently of each other.

Set screws provide only one of many different locking components that may be used to lock an apparatus according to the invention. In alternative embodiments, clips may be used. Such clips may have prongs or other features that are insertable into aligned holes of the two telescoping portions 298, 300. If desired, the telescoping portions 298, 300 may have multiple hole combinations that can be aligned at different relative positions of the telescoping members 298, 300 to permit locking of the telescoping portions 298, 300 at any of the relative positions.

According to another alternative embodiment, a locking component may include a rod (not shown) with ends that have rings or other features that can engage fixation members 80 independently. Such a rod may be attached to the two engagement members 80 parallel to the apparatus 270 to provide intervertebral fusion, or the apparatus 270 may even be removed to permit attachment of the rod in its place.

According to yet another alternative embodiment, a locking component may take the form of a curable resin, bone graft, or the like. Such a material may be injected into an apparatus 270 and allowed to harden to provide locking. Those of skill in the art will recognize that a variety of other locking components may be used. Similarly, many different structures may be used to lock the ends of an apparatus such as the apparatus 270 to restrict or prevent rotation of the ends with respect to the vertebrae 24, 26.

Returning to FIG. 10, in one specific example, the telescoping portion 298 of the first containment member 292 has an outside diameter of about 8 millimeters, and the telescoping portion 300 of the second containment member 294 has an outside diameter of about 7 millimeters. Upon assembly of the bridge 272 and the resilient rod 274, the centers of the mounting apertures 102 may be about 35 millimeters apart when the resilient section 338 is substantially undeflected. In use, the resilient section 338 may be expected to deflect by plus or minus about five millimeters.

The present invention may be embodied in other specific forms without departing from its spirit or essential characteristics. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stabilization system for controlling relative motion between a first vertebra and a second vertebra, the stabilization system comprising:
    a first stabilizer comprising:
        a resilient member configured to be coupled to extend along a path to transmit tension and compression between the first and second vertebrae;
        a first member having a substantially rigid construction, the first member extending along the path to keep the path substantially straight; and
        a locking component positionable to lock the first stabilizer to substantially prevent extension of the second vertebra with respect to the first vertebra.

2. The stabilization system of claim 1, wherein the first stabilizer comprises a second member that slidably engages the first member such that the first and second members cooperate to keep the path substantially straight.

3. The stabilization system of claim 2, wherein the second member telescopically engages the first member.

4. The stabilization system of claim 3, wherein the first and second members are hollow, wherein the resilient member is positioned within a cavity defined by engagement of the first and second members.

5. The stabilization system of claim 1, wherein the first member comprises an end attachable to a pedicle of one of the first vertebra and the second vertebra.

6. The stabilization system of claim 5, wherein the end is attachable to the pedicle such that the end can rotate about at least one axis with respect to the pedicle after attachment of the end to the pedicle.

7. The stabilization system of claim 5, further comprising a second stabilizer comprising:
    a second resilient member configured to be coupled to extend along a second path to transmit tension and compression between the first and second vertebrae; and
    a second member having a substantially rigid construction, the second member extending along the second path to keep the second path substantially straight;
    wherein the second member comprises a second end attachable to a second pedicle of one of the first vertebra and the second vertebra such that the first and second stabilizers are attachable in a generally symmetrical manner across a sagittal plane of the first and second vertebrae.

8. The stabilization system of claim 1, wherein the resilient member comprises a helical spring.

9. The stabilization system of claim 8, wherein the helical spring comprises a resilient portion and an end attachable to a pedicle of one of the first vertebra and the second vertebra, wherein the resilient portion and the end are integrally formed with each other.

10. The stabilization system of claim 1, wherein the first member is substantially coaxial with the resilient member.

11. The stabilization system of claim 10, wherein the resilient member comprises a resilient portion having a bore, wherein the first member extends through the bore along at least an entire length of the resilient member.

12. The stabilization system of claim 1, wherein the locking component is configured to cooperate with the first stabilizer to substantially prevent all relative motion of the first and second vertebrae.

13. The stabilization system of claim 1, further comprising a crosslink comprising:
    a first end coupled to the first stabilizer; and
    a second end extending from the first stabilizer, wherein the second end is substantially secured with respect to one of the first and second vertebrae to restrict axial rotation of the first vertebra with respect to the second vertebra.

14. A method for controlling relative motion between a first vertebra and a second vertebra, the method comprising:
    exposing at least a portion of the first and second vertebrae;
    positioning a resilient member to extend along a path to transmit tension and compression between the first and second vertebrae;
    positioning a first member having a substantially rigid construction to extend along the path to keep the path substantially straight; and
    positioning a locking component to lock the first stabilizer to substantially prevent extension of the second vertebra with respect to the first vertebra.

15. The method of claim 14, further comprising positioning a second member in telescopic engagement with the first member to extend along the path such that the first and second members cooperate to keep the path substantially straight, wherein the first and second members are hollow, wherein the resilient member is positioned within a cavity defined by engagement of the first and second members.

16. The method of claim 14, wherein the first member comprises an end, the method further comprising attaching the end to a pedicle of one of the first vertebra and the second vertebra.

17. The method of claim 16, wherein attaching the end to the pedicle comprises enabling the end to rotate about at least one axis with respect to the pedicle after attachment of the end to the pedicle.

18. The method of claim 16, further comprising:
    positioning a second resilient member to extend along a second path to transmit tension and compression between the first and second vertebrae; and
    positioning a second member having a substantially rigid construction to extend along the second path to keep the second path substantially straight;
    wherein positioning the second member comprises attaching a second end of the second member to a second pedicle of one of the first vertebra and the second vertebra such that the first and second members are attachable in a generally symmetrical manner across a sagittal plane of the first and second vertebrae.

19. The method of claim 14, wherein the resilient member comprises a helical spring comprising a resilient portion and an end integrally formed with the resilient portion, wherein positioning the first resilient member comprises attaching the end to a pedicle of one of the first vertebra and the second vertebra.

20. The method of claim 14, wherein the first member is substantially coaxial with the resilient member, wherein the resilient member comprises a resilient portion having a bore, wherein the first member extends through the bore along at least an entire length of the resilient member.

21. The method of claim 14, wherein the resilient member and the first member are incorporated into a first stabilizer, the method further comprising:
    coupling a first end of a crosslink to the first stabilizer; and
    substantially securing a second end of the crosslink with respect to one of the first and second vertebrae such that the second end extends from the stabilizer to restrict axial rotation of the first vertebra with respect to the second vertebra.

* * * * *